United States Patent [19]
Mori et al.

[11] Patent Number: 5,593,779
[45] Date of Patent: Jan. 14, 1997

[54] FIBER FOR CLOTHING AND PRODUCTION METHOD THEREFOR

[75] Inventors: Kazuo Mori; Kazunori Nishizawa; Yoshifumi Niki, all of Tochigi-ken, Japan

[73] Assignee: Kao Corporation, Tokyo, Japan

[21] Appl. No.: 476,581

[22] Filed: Jun. 7, 1995

[30] Foreign Application Priority Data

Jun. 15, 1994 [JP] Japan .................................. 6-133012
Mar. 30, 1995 [JP] Japan .................................. 7-072970

[51] Int. Cl.⁶ .................................. D02G 3/00
[52] U.S. Cl. .................. 428/375; 428/393; 435/179; 435/180; 435/176
[58] Field of Search .................. 428/375, 343; 435/179, 180, 176

[56] References Cited

U.S. PATENT DOCUMENTS

| | | | |
|---|---|---|---|
| 3,669,841 | 6/1972 | Miller | 435/176 |
| 3,824,150 | 7/1974 | Lilly et al. | 435/179 |
| 3,841,969 | 10/1974 | Emery et al. | 435/179 |
| 3,909,360 | 9/1975 | Horiuchi et al. | 435/179 |
| 4,013,514 | 3/1977 | Wildi et al. | 435/179 |
| 4,251,631 | 2/1981 | Simon | 435/176 |
| 4,356,267 | 10/1982 | Callegaro et al. | 435/179 |
| 4,371,612 | 2/1983 | Matsumoto et al. | 435/180 |
| 4,464,468 | 8/1984 | Avrameas et al. | 435/179 |
| 4,610,962 | 9/1986 | Takagi et al. | 435/179 |
| 4,749,653 | 6/1988 | Lee et al. | 435/180 |
| 4,845,035 | 7/1989 | Fanta et al. | 435/180 |
| 4,970,156 | 11/1990 | Avameas et al. | 435/179 |

FOREIGN PATENT DOCUMENTS

| | | |
|---|---|---|
| 0476915 | 3/1992 | European Pat. Off. . |
| 2200281 | 4/1974 | France . |
| 2204633 | 5/1974 | France . |
| 61-245374 | 10/1986 | Japan . |
| 3-199471 | 8/1991 | Japan . |
| 6-146173 | 5/1994 | Japan . |
| 889180 | 2/1962 | United Kingdom . |

*Primary Examiner*—Newton Edwards
*Attorney, Agent, or Firm*—Oblon, Spivak, McClelland, Maier & Neustadt, P.C.

[57] ABSTRACT

A fiber for clothing, the fiber having a layer of crosslinked enzyme protein on a surface of a single fiber or a monofilament thereof; and a method for producing the fiber for clothing having the steps of immersing a fiber into a solution containing an enzyme protein to adsorb the enzyme protein onto a surface of a single fiber or a monofilament thereof, and crosslinking the enzyme protein adsorbed on the surface of the single fiber or the monofilament with a crosslinking agent.

9 Claims, 8 Drawing Sheets

FIG. 3A  1 μm
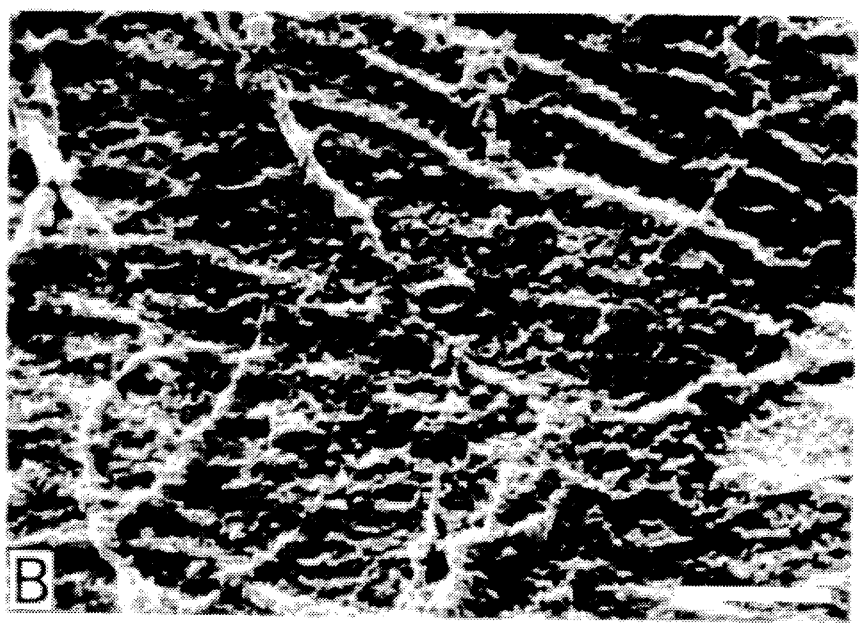
FIG. 3B  1 μm

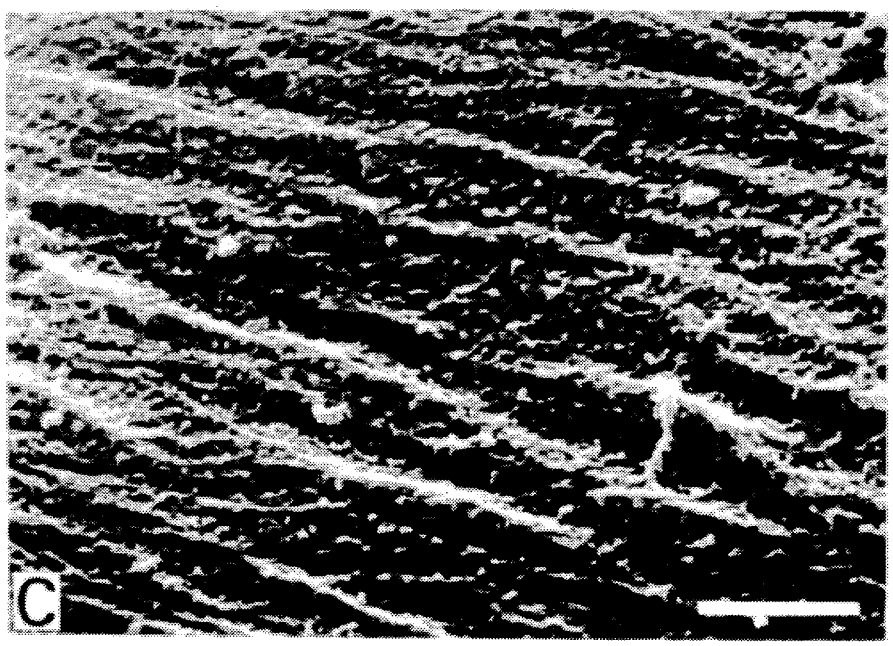
FIG. 3C  1 μm

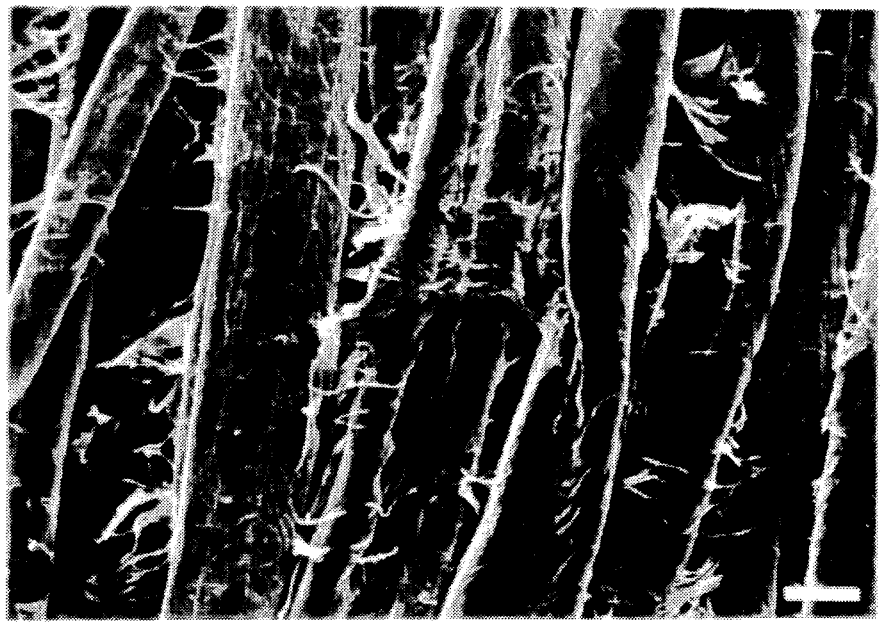
FIG.5A  10 µm
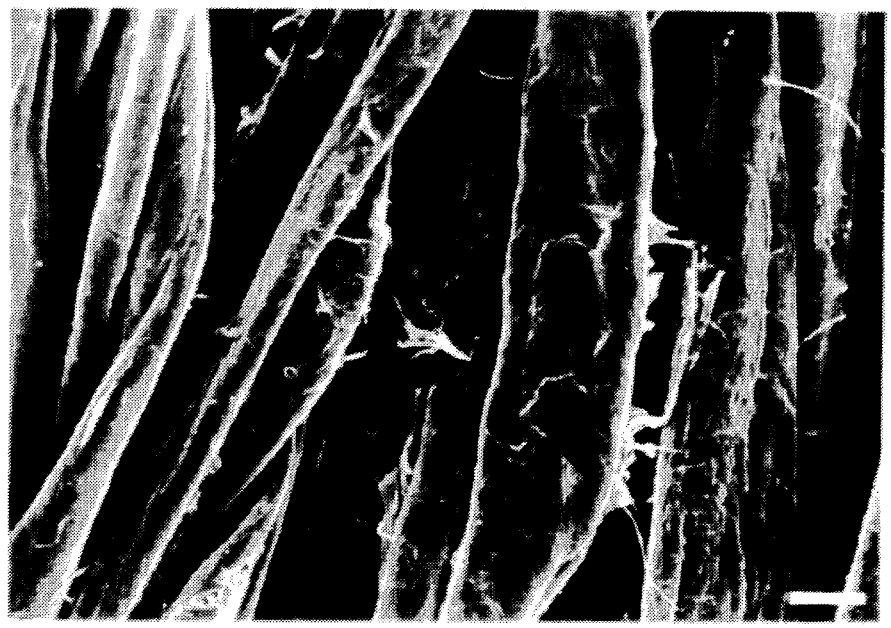
FIG.5B  10 µm

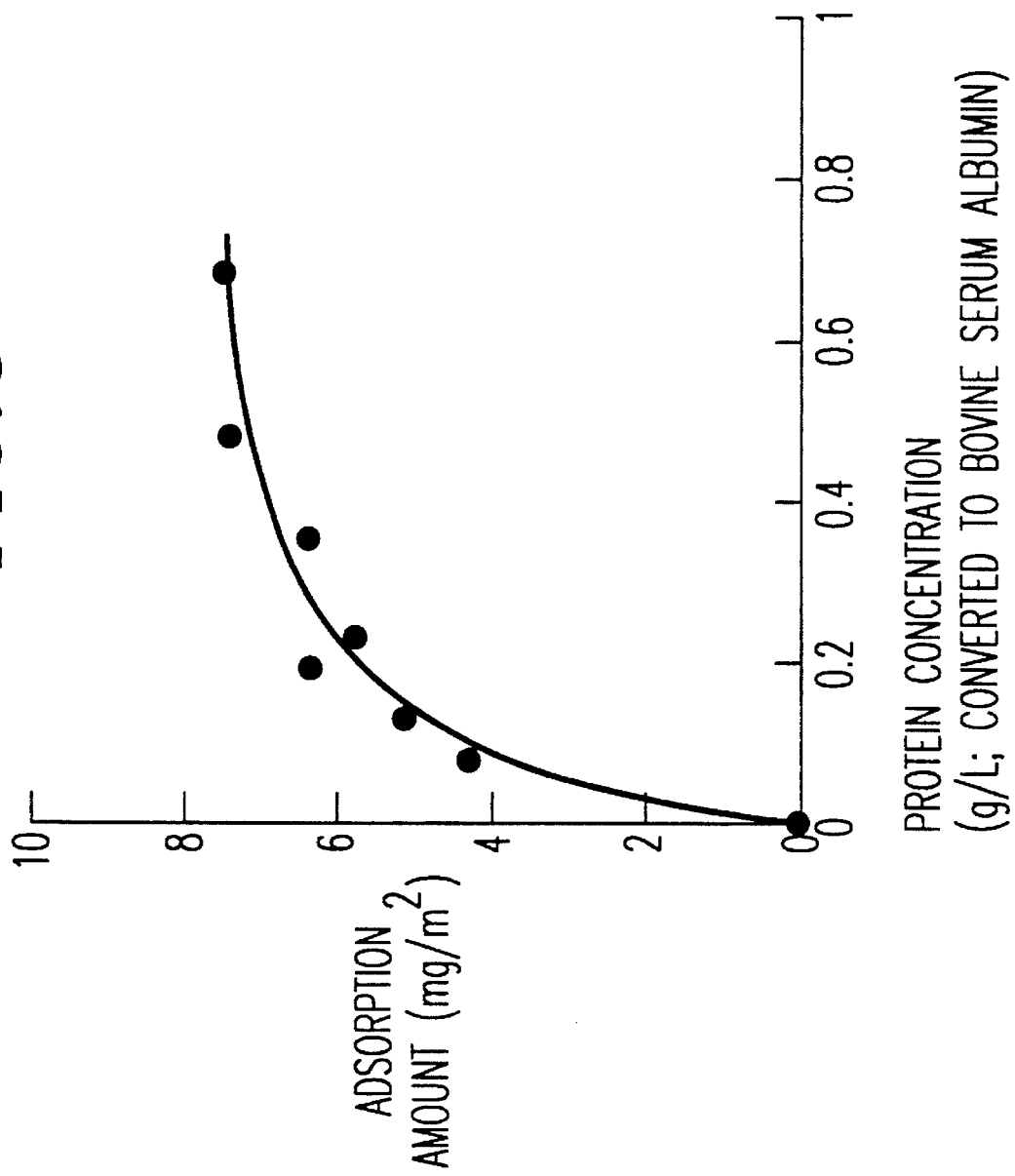

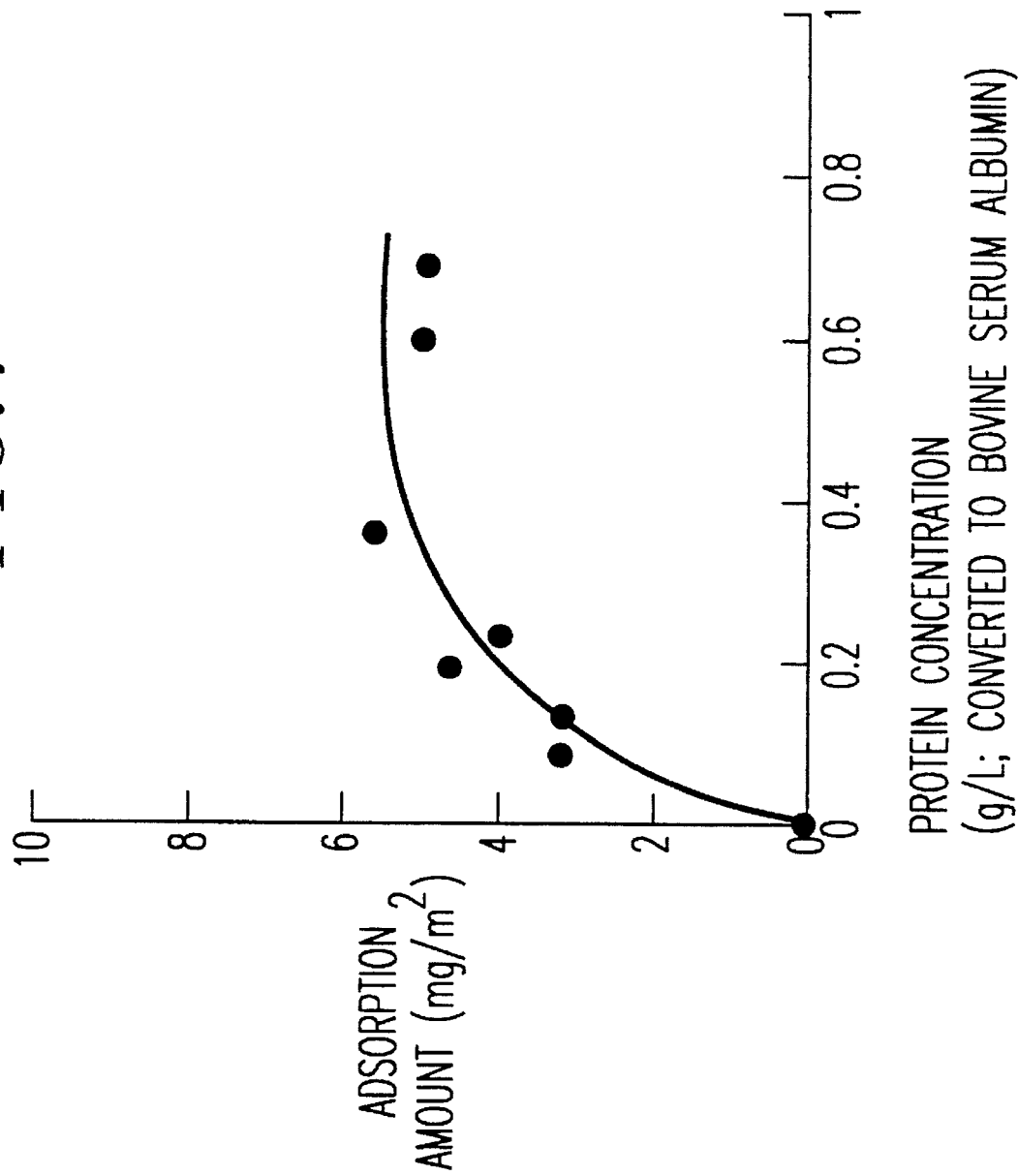

FIBER FOR CLOTHING AND PRODUCTION METHOD THEREFOR

BACKGROUND OF THE INVENTION

1. Field of the Invention

The present invention relates to a fiber for clothing. Specifically, the present invention relates to a novel cellulosic fiber or a novel synthetic fiber, whose monofilament is covered with a crosslinked enzyme protein layer on the surface thereof: and to a production method of the fiber.

2. Discussion of the Related Art

Feeling, strength, hygroscopicity, and other physical properties of a natural cellulose such as cotton and hemp, and a regenerated cellulose such as viscose rayon are closely associated with the internal structure of their monofilament made up of cellulose molecules, such as crystallinity (degree and orientation of crystallization) and lamella structure (micro-fibril and fibril). When a cellulosic fiber is chemically treated, not only the surface but also the internal structure of its monofilament are affected, which may in some cases impair advantageous properties of the original cellulosic fiber.

If only the surface of a monofilament can be modified without changing the internal structure thereof, novel functions can be added to the fiber without varying the properties proper to a cellulosic fiber. Such novel functions can add a great value to a cellulosic fiber in developing their applications for clothing.

For selectively improving the monofilament surface of a cellulosic fiber, there have been proposed a number of methods wherein a protein with a molecular weight that is too high to penetrate the monofilament is used to form a protein layer selectively on the single monofilament surface.

For example, a natural cellulose fiber is immersed in a dilute solution of a water-soluble protein to adhere the protein onto the fiber's surface, followed by binding the fiber and the protein by crosslinking, to form a protein Layer on the fiber's surface (Japanese Patent Laid-Open No. 61-245374).

However, these methods are faulty in that the protein adheres unevenly to the single fiber surface, failing to give an even layer over the entire yarn. In fact, when a fiber on which a protein layer has been formed by the above-described method is dyed with an acid dye, uneven dyeing occurs over the entire yarn, indicating that even protein layer is not obtained on each fiber surface of the yarn.

A natural cellulose fiber, and a regenerated cellulose fiber such as viscose rayon show fibrillation on the monofilament surface after repeated wearing and washing, which can result in fuzz and pilling. Such fuzz and pilling can alter cloth feeling and, in some cases, deteriorate the feeling due to hardening. Other undesirable changes caused by fuzz and pilling include luster reduction. To prevent the deterioration of feeling and the reduction of luster in these fibers, it is necessary to prevent fuzz and pilling and suppress fibrillation, a cause of fuzz and pilling.

Conventional techniques for suppressing fibrillation include the method in which a fiber is swollen by immersing a fabric of the fiber in an aqueous solution of a caustic alkali, and the method in which the cloth is treated with a crosslinking reagent for cellulose (e.g., urea-formalin resin, melamine resin, glyoxal resin) (Japanese Patent Laid-Open No. 62-85082).

The above methods are effective in suppressing the fibrillation on the monofilament surface and keeping luster of the fiber. However, the treatment with a crosslinking reagent for cellulose causes a structural change due to cellulose-to-cellulose crosslinking within a single fiber/monofilament. This results in a change in feeling, and, in some cases deterioration of feeling. Therefore, in order to suppress fibrillation without impairing feeling of the fiber, a cellulosic fiber whose monofilament surface is selectively modified without changing internal structure, and a method for such modification have been sought.

On the other hand, synthetic fibers are less comfortable to the wearer in terms of feeling and touch in comparison with natural fibers, such as wool and silk. This is attributable to the fact that a petroleum-based synthetic fiber has low water absorbency and hygroscopicity compared with a natural fiber, because the surface of the fiber is hydrophobic, although they have excellent mechanical strength and other good properties. As solution to these problems, various chemical treatments have been performed to give hydrophilicity to synthetic fibers. For example, a hydrophilic group, such as the hydroxyl group, amino group and carboxyl group, is introduced to the monofilament surface by a chemical reaction, or the monofilament surface is made porous by a plasma treatment. However, the former method is faulty in that overreaction can result in considerably reduced fiber strength, because reaction control during the treatment of the monofilament surface is difficult. The latter method has a problem that it requires large-scale equipment. It is also possible to give hydrophilicity to a synthetic fiber by immobilizing a substance having a hydrophilic group onto the surface of constituent fibers of a synthetic fiber using a crosslinking agent. One such method, for example, uses a polyamino acid and a crosslinking agent to form a layer on the synthetic fiber surface to give hydrophilicity (Japanese Patent Laid-Open NO. 3-199471).

In the above method, however, it is difficult to form a layer of polyamino acid having a constant molecular weight by controlling polyamino acid polymerization. Therefore, the layer is likely to form not only on the monofilament surface but also over the yarn or even over the entire cloth, depending on molecular weight, so that the flexibility of fiber is very restricted even though hydrophilicity can be given to the fiber, resulting in deterioration of feeling due to fiber hardening. It is therefore important that the treatment to give hydrophilicity does not expand beyond the level of a monofilament of a yarn. So, there is a need of an appropriately modified synthetic fiber and a method for such modification.

SUMMARY OF THE INVENTION

In the above situation, the present inventors studied to form a uniform protein layer on the single fiber/monofilament surface of a cellulosic fiber, by adsorption of protein onto the fiber surface, rather than by adhesion. As a result, the inventors found that a protein can be adsorbed onto the monofilament surface of a cellulosic fiber by immersing the fiber in a solution containing the protein under particular conditions, and that the protein is exhausted from the solution and adsorbed onto the fiber, with almost no portion remaining in the solution, so that an even uniform protein adsorption layer is formed on the surface of each monofilament of the yarn without protein retention in the capillary gaps between monofilaments even when the solution remains in the gaps. The inventors also found that enzyme proteins surprisingly show high adsorbability to a cellulosic fiber, and that the enzyme protein adsorbed onto the monofilament surface can be prevented from being desorbed from the surface by washing or other external forces, permitting the obtainment of a cellulosic fiber suitable for clothing, by crosslinking the enzyme protein adsorbed on the cellulosic monofilament, for example, using a crosslinking agent. The present inventors also found that, under the same conditions as described above, a uniform protein layer can be formed only on the surface of a monofilament of a synthetic fiber by immersing the fiber in a solution containing the protein and crosslinking the resulting protein adsorption layer with a crosslinking agent. The protein adsorption layer has effects of preventing fibrillation of cellulosic fibers and giving hydrophilicity to synthetic fibers. The layer can endure repeated washing and retain the effects for a long period of time, and, therefore, fibers suitable for clothing can be obtained.

Accordingly, an object of the present invention is to provide a cellulosic fiber or a synthetic fiber for clothing wherein an enzyme protein adsorption layer crosslinked is formed on the surface of a monofilament.

Another object of the present invention is to provide a method for producing the above fiber for clothing, comprising the steps of:

immersing a cellulosic fiber or a synthetic fiber in a solution containing an enzyme protein to adsorb the protein onto the surface of the monofilament of the fiber; and crosslinking the enzyme protein to form crosslinkages.

BRIEF DESCRIPTION OF THE DRAWINGS

The present invention will become more fully understood from the detailed description given hereinbelow and the accompanying drawings which are given by way of illustration only, and thus, are not limitative of the present invention, and wherein:

FIGS. 3(A) to 3(C) are microphotographs showing the surface of cellulosic single fibers in Example 2, wherein FIG. 3(A) is the surface of untreated single fibers; FIG. 3(B) is the surface of single fibers with a crosslinked enzyme protein adsorption layer before washing; and FIG. 3(C) is the surface of single fibers with a crosslinked enzyme protein adsorption layer after 20 cycles of washing.

FIGS. 5(A) and 5(B) are microphotographs showing the surface of single fibers of natural cellulose in Example 4, wherein FIG. 5(A) is the surface of untreated fibers after 20 cycles of washing, and FIG. 5(B) is the surface of fibers with a crosslinked enzyme protein adsorption layer after 20 cycles of washing.

FIG. 6 is a graph showing the relation between protein concentration and amount of protein adsorbed in Example 5.

FIG. 7 is a graph showing the relation between protein concentration and amount of protein adsorbed in Example 6.

DETAILED DESCRIPTION OF THE INVENTION

Figure 1:
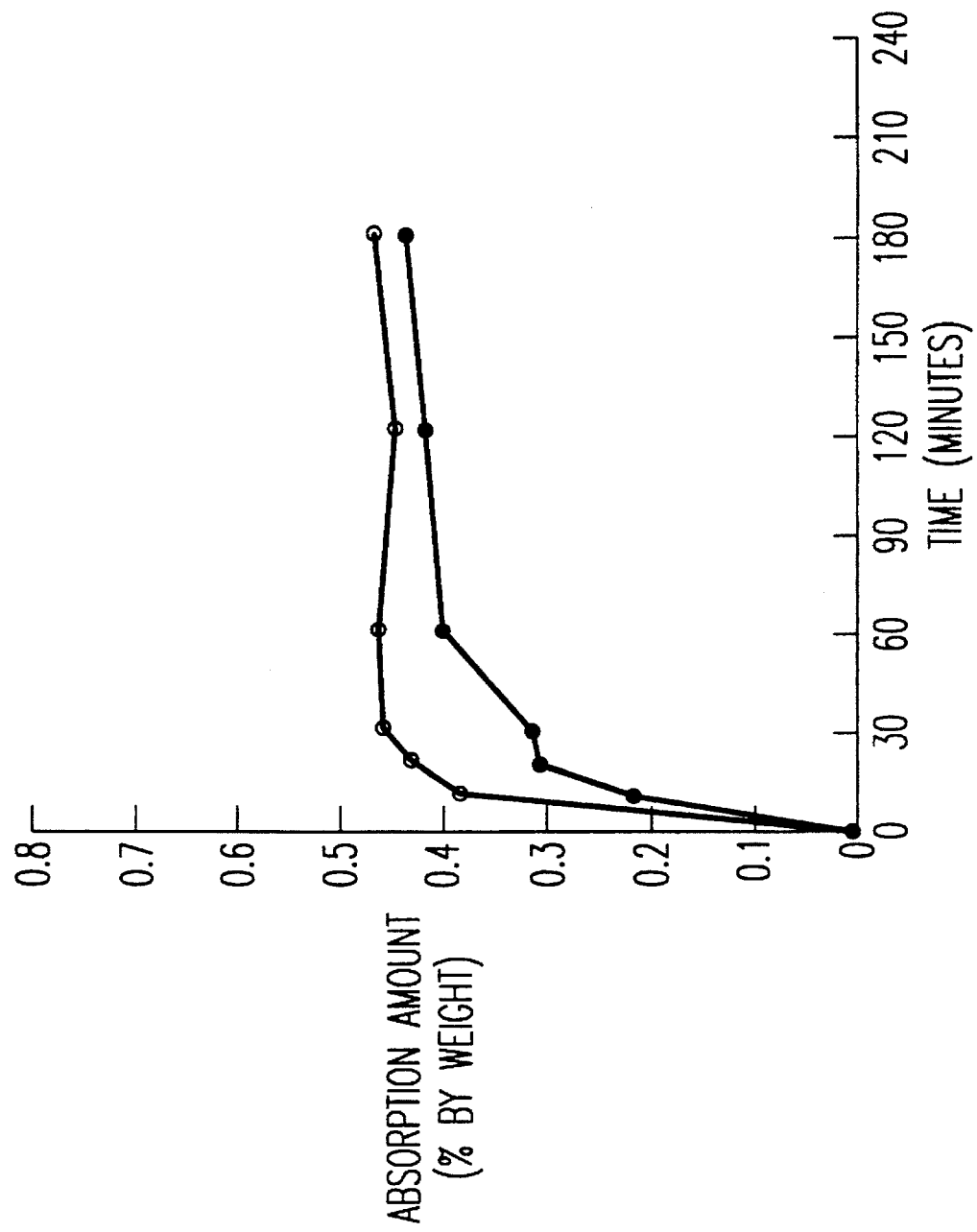
FIG. 1 is a graph showing time-course change in the amount of enzyme protein adsorbed onto fibers in Example 1, wherein ● represents cellulase produced by a Bacillus sp., and o represents cellulase produced by a Trichoderma sp.

Of cellulosic fibers, examples of natural cellulose fibers to which the present invention is applicable are cotton, hemp, and other cellulose-based natural fibers, including treated fibers such as cotton fibers mercerized with NaOH, KOH, LiOH, or the like, and cotton fibers treated with liquid ammonia. When immersing a natural cellulose fiber, in the form of a yarn, textile fabric, or nonwoven fabric, in a dilute enzyme protein solution as described later to adsorb the enzyme protein onto the single fiber surface, it does not matter that yarn or fabric to be treated contains a synthetic fiber or other fibers than a natural cellulose fiber.

Examples of regenerated cellulose fibers to which the present invention is applicable include viscose rayon, cupra, and TENCEL manufactured by Courtauls PLC. Examples of synthetic fibers include polyester, acrylic, nylon, vinylon, polypropylene, polyethylene, polyvinyl chloride, vinylidene, polyurethane and benzoate. When immersing these fibers, in the form of a yarn, textile fabric, or nonwoven fabric, in a dilute enzyme protein solution to adsorb the enzyme protein onto the monofilament surface of the fibers, the yarn or fabric may be a mixture of natural and chemical fibers.

Enzyme proteins used in the present invention are those generically defined as a class of proteins having a particular structure for catalytic action. In other words, all proteins that possess a structure for catalytic action can be used, whether or not they exhibit catalytic action. When proteins other than enzyme proteins are used, the effects of the present invention may be obtained to some extent, but sufficient effect may not be achieved.

Enzyme proteins have different biological origins: animal, plant and microbial origins. Enzyme proteins of any origin are usable for the present invention.

Such enzyme proteins, as classified on the basis of enzyme reaction type, include hydrolases, lyases, oxidoreductases, ligases, transferases and isomerases, all of which are usable for the present invention. A preference is given to hydrolases, exemplified by proteases (peptidase), glucosidases such as cellulase and amylase, and esterases such as lipase.

The molecular weight of the enzyme protein is preferably not lower than 10,000, more preferably in the range of from 20,000 to 300,000. Being not lower than 10,000 in molecular weight, most enzyme proteins cannot penetrate the monofilament (lamella structure) of cellulosic fibers such as a natural cellulose fiber and rayon. Also, they cannot penetrate the monofilament of synthetic fibers, because the monofilament internal structure is dense. Enzyme adsorption sites of cellulosic fibers and synthetic fibers are therefore limited to the surface of the monofilament.

In the present invention, one or more enzyme proteins can be used in combination. It is unnecessary to use an expensive purified enzyme protein, because the presence of a protein other than enzyme proteins in the dilute protein solution does not cause any problem. This is because the enzyme protein is preferentially adsorbed onto the monofilament surface due to their high adsorbability.

The methods for crosslinking in the present invention are not limited, and those using a crosslinking agent, electron beam, UV ray, a peptide synthesizing reagent, or heat may be used [Shiro AKABORI, et al. Protein Chemistry, pp. 395–397 & pp. 509–565 (Kyoritsu Shuppan)]. Crosslinking agents usable in the present invention include those reactive mainly with functional groups in protein. Any crosslinking agents may be used as long as they can make crosslinkages in an intermolecular or intramolecular reaction in the protein. For example, known crosslinking agents, such as those described in "Shin Seikagaku Jikken Koza 1, Protein IV, Structure-Function Correlation, Chap. 13, Crosslinking, pp. 207–254 (Tokyo Kagaku Dojin)" and "Seibutsu Kagaku Jikkenho 13, Chemical Modification of Protein Vol. 2, Chap. VI, Crosslinking Reaction, pp. 81–113, by Motonori Ohno (Gakkai Shuppan Center)" can be used. Because of high reactivity, aldehyde compounds, epoxy compounds, and isocyanate compounds are preferably used. Known aldehyde compounds can be used widely for the present invention, including formaldehyde, and dialdehydes such as glyoxal, malonaldehyde and glutaraldehyde. Usable epoxy compounds include mono- and poly-glycidyl ethers of ethylene glycol, polyethylene glycol, propylene glycol, polypropylene glycol, glycerol, sorbitol, polyglycerol, pentaerythritol, tris(2-hydroxyethyl) isocyanurate, trimethylolpropane, neopentylglycol, phenol ethylene oxide, or lauryl alcohol ethylene oxide; and epoxy-group-containing coupling agents. These epoxy compounds are normally used in aqueous solution, but epoxy compounds with low solubility in water are preferably dissolved in a mixture of a small amount of an organic solvent such as dioxane and isopropyl alcohol, and water.

Usable isocyanate compounds include those having two or more isocyanate groups in the molecule thereof, examples of which are toluene diisocyanate, diphenylmethane diisocyanate, hexamethylene diisocyanate, isophorone diisocyanate and naphthalene diisocyanate. These isocyanate compounds are preferably used by dissolving in a known organic solvent such as chloroform, hexane and toluene which permit crosslinking with protein.

The method for producing the fiber for clothing of the present invention will now be described. First, a cellulosic fiber or a synthetic fiber is immersed in a dilute solution of an enzyme protein. To efficiently adsorb the enzyme protein onto the fiber, the solution is preferably shaken or stirred.

The diluent for enzyme protein is preferably an acidic, neutral or weakly alkaline buffer having a pH in the range of from 1 to 10. Such a buffer is used to dilute enzyme protein as well as to adjust solution pH. The dilute solution is preferably prepared to have an acidic to neutral pH value between 3 and 8, considering the adsorption conditions of an enzyme protein to the fiber. The temperature of the dilute solution is preferably not higher than 60° C., the critical temperature of protein thermal denaturation. More preferably, the process of enzyme protein adsorption is carried out below room temperature, normally below 20° C. When a natural cellulose fiber or a regenerated cellulose fiber such as rayon is treated with an enzyme such as cellulase which hydrolyses cellulose fibers, the treatment is preferably performed at a low temperature in the range of from 0° to 10° C., more preferably 0° to 5° C. The ionic strength of the dilute solution is preferably not lower than 0.01, more preferably in the range of from 0.05 to 0.2 to maintain a sufficient pH buffering capability of the buffer. In the method of the present invention, the enzyme protein concentration in the dilute solution may be low, since an adsorption layer is formed on the single fiber/monofilament surface by adsorption of an enzyme protein. The enzyme protein concentration is preferably such that the adsorbed amount of enzyme protein is 0.2–1% by weight (hereinafter simply expressed as %) based on the weight of the monofilament, or 3–15 mg/m² per unit surface area of the fiber.

The duration of fiber immersion in the dilute enzyme protein solution can be the time to reach the adsorption equilibrium. This immersion is preferably carried out under conditions showing Langmuir's adsorption isotherm based on monomolecular adsorption with respect to the relationship between the enzyme protein concentration in the aqueous solution and the amount of protein adsorbed to the fiber. In determining the time to adsorption equilibrium of an enzyme protein or plotting the adsorption isotherm thereof, the amount of enzyme protein adsorbed can be approximated by measuring the change of protein concentration in the solution due to adsorption of the protein to the fiber, and applying the pre- and post-adsorption protein contents (enzyme concentrations) in the solution and the amount of fiber used to the equation (1) below, or applying the pre- and post-adsorption protein contents, the specific surface area of fiber, and the amount of fiber used to the equation (1') below. The protein content in the aqueous solution is determined by the Lowry method (DC-protein assay method; BIO-RAD), the most commonly used protein assay method, using a standard curve of bovine serum albumin, and is expressed on the basis of bovine serum albumin. The amount of protein adsorbed to the fiber is expressed in % by weight, or in mg/m² by calculating specific surface area of the fiber by the BET multiple-point method based on krypton adsorption to determine the amount of protein adsorbed per unit surface area of the fiber.

$$\text{Adsorption amount} = [(X_A - X_B) \times (V/W)] \times 100 \quad (1)$$

(% by weight)

$$\text{Adsorption amount} = [(X_A - X_B) \times (V/W)] / S \times 1000 \quad (1')$$

(mg/m²)

wherein W means the amount of fiber used (g); V means the amount of enzyme solution (L); $X_A$ means the concentration of enzyme in solution before adsorption (g/L); $X_B$ means the concentration of enzyme in solution after adsorption (g/L); and S means the specific surface area of the fiber used (m²/g).

The concentration of an enzyme protein in the solution depends on the amount of fiber to be treated, and it is normally sufficient to use a concentration to achieve an adsorption equilibrium.

After an enzyme protein is adsorbed onto a cellulosic fiber or a synthetic fiber as described above, a crosslinking treatment is performed using a crosslinking agent, or the like. This treatment may be performed in the same solution without drying the fiber after adsorption, and may be performed in another solution. The treatment may also be performed after the fiber is taken out from the solution and dried. Crosslinking agent concentration varies depending on functional group equivalent (molecular weight/functional group number). The amount of crosslinking agent used can be decided according to the total molar number of functional groups calculated from the amount of protein adsorbed per unit weight of the fiber. Temperature for the crosslinking reaction is set according to the crosslinking agent used, and the reaction is preferably carried out at a weakly acidic to weakly alkaline pH.

It is also required that the crosslinking reaction is carried out under conditions which do not adversely affect the state of protein adsorption achieved in the preceding treatment. Aldehyde compounds (crosslinking agents), for example, are capable of easily reacting with the amino group of protein at room temperature, and forming crosslinkage while maintaining the state of protein adsorption. In contrast, in case of epoxy compounds (crosslinking agents), warming or heating is applied to promote their reaction with the amino or carboxyl group in protein. Although warming or heating can thermally denature the protein, an epoxy compound can be used, as long as the uniformity of the protein adsorption layer on the monofilament surface is retained. The crosslinking agent treatment is followed by thorough washing with water or hot water by a conventional method.

It is preferable that the adsorption layer of an enzyme protein crosslinked on the monofilament surface of a cellulosic fiber or a synthetic fiber be enzymatically inactive at the time when the fiber with the protein adsorption layer is used as a fabric for clothing (wearing). Normally, the enzyme is almost inactivated at the crosslinking stage. If some enzyme activity remains, it is preferable to remove the activity.

The adsorption layer of a crosslinked enzyme protein shows no protein desorption even after 20 cycles of washing with a household washing machine, as confirmed by dyeing with a protein-dyeing dye, demonstrating increased durability against washing was obtained by crosslinking. As for changes of fiber properties, the fiber with an adsorption layer shows exactly the same hygroscopicity as untreated fibers.

The adsorption layer formed on the monofilament surface also serves to protect the internal structure of the single fiber/monofilament against externally applied physical or chemical stimulation. For example, the adsorption layer suppresses fuzz (fibrillation) on the monofilament surface due to washing by protecting internal structure of a fiber from physical stimulation such as washing machine water flow. The adsorption layer thus provides fibers for clothing with durability for long-term use.

Moreover, the protein adsorption layer can be chemically modified by a chemical treatment. Specifically, a substance having new function can be bound to functional groups of protein or unreacted functional groups in crosslinking agents. For example, functional groups in protein can be made to react with a dye for protein fibers such as wool and silk, after crosslinking of an adsorption layer (enzyme protein). In this case, unevenness-free dyeing can be achieved. Though cotton fiber is known to be difficult to dye, for example, it becomes possible to dye cotton fiber dense by modifying the surface of the fiber by the present method. Also, it becomes possible to dye cotton fiber easily and effectively with an acidic dye. When an epoxy compound is used as the crosslinking agent, its functional groups which remain unchanged after crosslinking reaction can be made to react with a long-chain alkylamide by making use of the high reactivity of the epoxy group with the amide group. As a result, fibers having flexibility are obtained.

According to the method of the present invention, a cellulosic fiber for clothing and a synthetic fiber for clothing, both having a uniform enzyme protein layer on the surface of their single fiber/monofilament, can be obtained without affecting the internal structure of the monofilament. In the method of the present invention, the amount of protein enzyme required for the treatment is remarkably small, and so is the waste of the protein solution. Therefore, the present method is useful for production on an industrial scale in terms of efficiency and environmental protection.

EXAMPLES

The present invention is hereinafter described in more details by means of the following working examples, but the present invention is not limited by them.

Example 1

The enzyme proteins used were cellulase (molecular weight by SDS-PAGE: 100,000 and 130,000) produced by a Bacillus species (FERM-BP 1485) and cellulase (molecular weight by SDS-PAGE: 30,000 to 40,000; Meicelase TP-60, Meiji Seika Co., Ltd.) produced by a Trichoderma species, both used after ammonium sulfate precipitation, dialysis and lyophilization. The other proteins than enzyme proteins used were casein (account of Hammarsten, Wako Pure Chemical Industries, Ltd.) and albumin (bovine, Wako Pure Chemical Industries, Ltd.). As a natural cellulose fiber, a plain weave heavy shirting 1125 of cotton fiber (Laundry Research Association) was used.

The buffers used (special grade, Wako Pure Chemical Industries, Ltd.) were 100 mM acetic acid-sodium acetate buffer (pH 5) for acidic pH, and 50 mM disodium hydrogenphosphate-potassium dihydrogenphosphate buffer (pH 7) for neutral pH, both used at an ionic strength of 0.1.

First, the enzyme and other proteins were each diluted with each buffer. Protein concentrations, calculated as bovine serum albumin determined by the Lowry method, were set within the range of from 0 to 1 g/L. Next, the fiber, 50 g per liter of a protein solution, was completely immersed in the solution. While the solution was shaken at 5° C., immersion was continued until an adsorption equilibrium was reached. Time courses to adsorption equilibrium are shown in FIG. 1 (data on cellulase produced by a Bacillus sp. and cellulase produced by a Trichoderma sp.). In any case, an equilibrium was reached within 1 hour.

Figure 2:
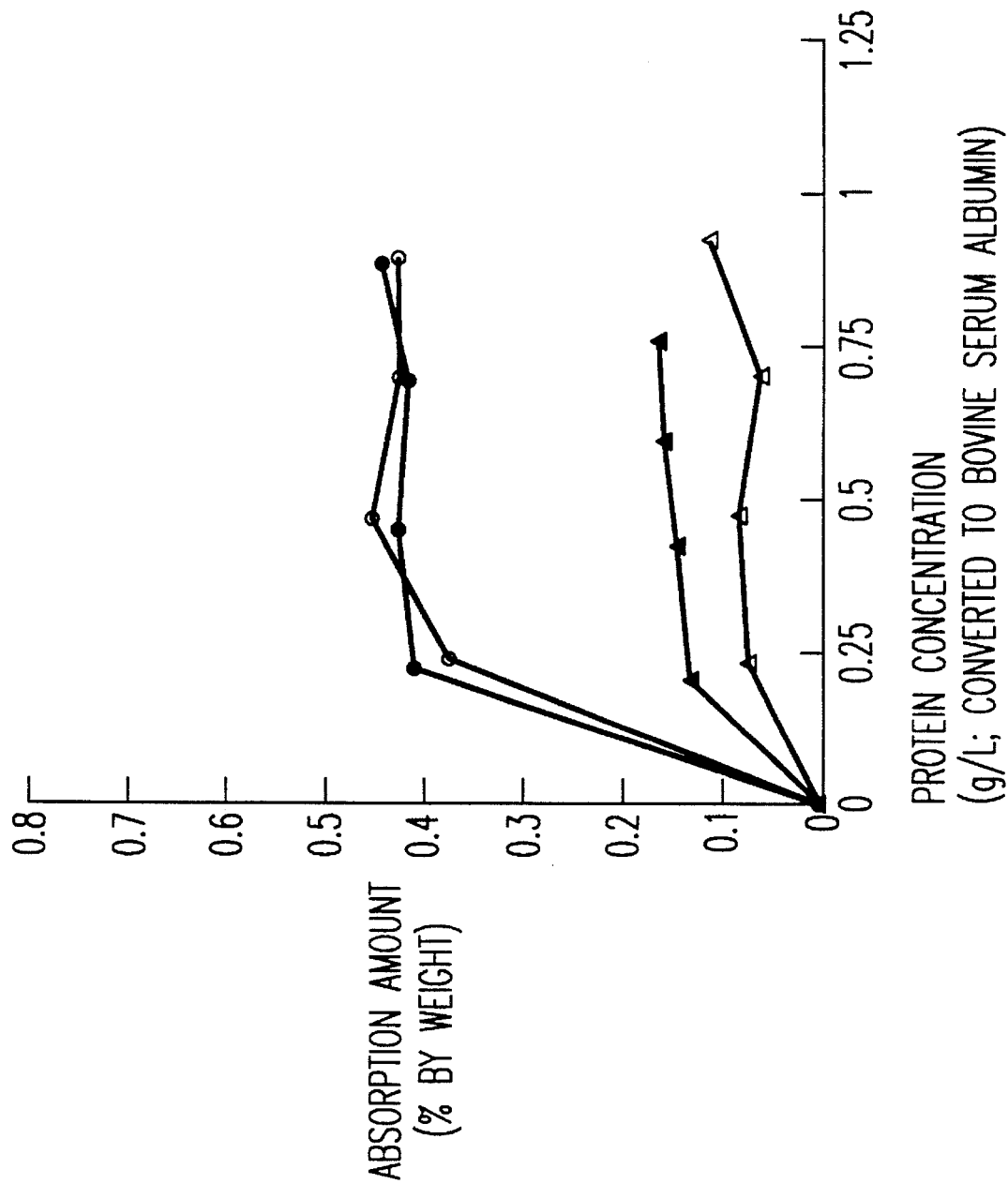
FIG. 2 is a graph showing the relation between protein concentration and amount of protein adsorbed in Example 1, wherein ● represents cellulase produced by a Bacillus sp.; o represents cellulase produced by Trichoderma sp.; ▲ represents casein; and △ represents albumin.

The adsorption isotherms plotted at a suitable pH for each protein are shown in FIG. 2. Adsorption isotherm plotting reveals that both the enzyme proteins, Bacillus cellulase and Trichoderma cellulase, show Langmuir's adsorption isotherm at an acidic pH of 5, demonstrating high adsorbability. The saturated adsorption amounts of both enzyme proteins were 0.4% of the fiber weight. As for proteins other than enzyme proteins, adsorption was peaked at pH 7 for casein and at pH 5 for albumin, showing the maximum adsorption amount of less than 0.2%.

Example 2

The enzyme protein used was cellulase produced by a Bacillus sp. (FERM-BP 1485), and the natural cellulose fiber used was plain weave heavy shirting 1125 of cotton fiber (Laundry Research Association).

First, the enzyme protein was diluted with 100 mM acetic acid-sodium acetate buffer. The concentration of the enzyme protein, calculated as bovine serum albumin as determined by the Lowry method, was set at 0.5 g/L. Next, the fiber, 50 g per liter of an enzyme protein solution, was completely immersed in the solution. While the solution was shaken at 5° C., immersion was continued for 3 hours until an adsorption equilibrium was reached.

Glutaraldehyde (about 25% solution, 1st grade, Wako Pure Chemical Industries, Ltd.) was used as a crosslinking agent of aldehyde-series, and polyglycerol polyglycidyl ether (DENACOL EX-521, Nagase Chemicals Ltd.), as an epoxy-series crosslinking agent. The latter is a compound represented by the formula shown below and having an average molecular weight of about 1,000 and an average epoxy equivalent of 172.

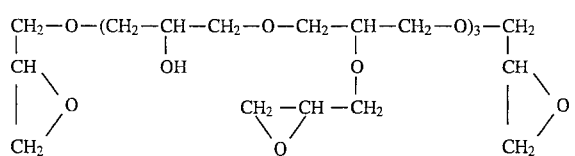

Each crosslinking agent was diluted to make a 100 mM solution with acetic acid-sodium acetate buffer; and the fiber, previously adsorbed with an enzyme protein, was immersed in the diluted solution of the crosslinking agent at 50 g per liter of the solution. The glutaraldehyde solution was shaken at 20° C. for 1 hour to carry out the crosslinking reaction. The DENACOL EX-521 solution was heated from 20° C. to 90° C. within 10 minutes, and carried out crosslinking reaction with shaking for 1 hour. After completion of the crosslinking treatment, the fiber was thoroughly washed with water and dried.

In order to evaluate the stability of the protein adsorption layer to detergent, washing with a household washing machine was performed using a model detergent of the composition shown in Table 1.

TABLE 1

| Components | Content (%) |
|---|---|
| Linear Sodium Alkylbenzenesulfonate | 25 |
| Sodium Alkylsulfate | 10 |
| Polyoxyethylene Alkyl ether | 2.5 |
| Sodium Hardened Beef Tallow Fatty Acid | 2.5 |
| Polyethylene Glycol | 1.5 |
| Sodium Polyacrylate | 1.5 |
| Crystalline Sodium Aluminosilicate (4A ZEOLITE) | 25 |
| Sodium Silicate | 10 |
| Sodium Carbonate | 10 |
| Sodium sulfate | Balance |
| Total | 100 |

The detergent was dissolved in tap water at 0.0833% (w/v). At a bath ratio to fiber of 1:30, the fiber was washed at 20° C. for 12 minutes using a household washing machine (SHIZUKA GOZEN, manufactured by Hitachi, Ltd.), followed by 5 minutes of rinsing, dehydration and drying. This washing process was repeated in 1, 5, 10 and 20 cycles.

The stability of a protein adsorption layer to washing can be determined by extracting the protein from the fiber before and after washing (0.5 N NaOH, 90° C., 1 hour) and assaying the amount of protein desorbed from the fiber due to washing by the Lowry method. In the case where a crosslinkage was made with a crosslinking agent, however, it is difficult to extract protein from the fiber, making it impossible to determine the amount of the protein. So, in such case, the fiber after the above washing process was dyed with a dye for protein, Coomassie Brilliant Blue (Quick CBB for electrophoresis, Wako Pure Chemical Industries, Ltd.), and the amount of residual protein was estimated from the dyeability.

Before washing, there was almost no difference in dyeability among the differently treated fibers: the fiber with an enzyme protein adsorption layer, the fiber heated at 90° C. for 1 hour after enzyme protein adsorption, and the fiber subjected to crosslinking treatment after enzyme protein adsorption. The amount of protein per unit fiber weight extracted from the fiber having an enzyme protein adsorption layer and the amount of protein extracted from the fiber heated after adsorption of an enzyme protein were found to be about 0.4%. A similar protein amount was noted in the fiber subjected to crosslinking treatment after enzyme protein adsorption. When the fiber heated after enzyme protein adsorption was subjected to 1 cycle of washing, the protein amount halved to about 0.2% per unit fiber weight. The amounts of residual protein in these fibers after washing were assessed from dyeability, using the criteria shown below. The results are shown in Table 2.

(Evaluation criteria)

⊚: showing a dyeability almost equal to the dyeability of a fiber having an enzyme protein adsorption layer where a protein resides in an amount of 0.4% per unit fiber weight.

o: showing a dyeability corresponding to a protein amount of not more than 0.4% and not less than 0.2% per unit fiber weight.

Δ: showing a dyeability corresponding to a protein amount of less than 0.2% per unit fiber weight.

x: showing no dyeability (i.e., no residual protein)

TABLE 2

| | Crosslinking agent | No. of washings | | | | |
|---|---|---|---|---|---|---|
| | | 0 | 1 | 5 | 10 | 20 |
| Comparative Examples (Untreated fiber) | No crosslinking (only adsorption) | ⊚ (0.41) | Δ (0.10) | x (<0.01) | x (<0.01) | x (<0.01) |
| | No crosslinking (heated at 90° C. for 1 hour) | ⊚ (0.43) | o (0.21) | Δ (0.08) | x (<0.01) | x (<0.01) |
| Inventive Examples | Glutaraldehyde (100 mM, Room Temperature, 1 hour) | ⊚ | ⊚ | ⊚ | ⊚ | ⊚ |
| | DENACOL EX-521 (100 mM, 90° C., 1 hour) | ⊚ | ⊚ | ⊚ | ⊚ | ⊚ |

*Residual amount of protein (% by weight) is in parentheses.

It is evident from Table 2 that the fibers with an enzyme protein adsorption layer that was not subjected to crosslinking treatment did not show any protein dyeability after 5 cycles of washing, showing almost no residual protein. In contrast, the fiber subjected to crosslinking treatment showed almost no loss of dyeability even after 10 or 20 cycles of washing, demonstrating that no protein was desorbed by washing.

The above-treated fibers were examined for the condition of the enzyme protein adsorption layer on the single fiber surface using a scanning electron microscopy (field emission scanning electron microscope, FE-SEM S-4000, Hitachi, Ltd.).

The fiber to be tested, fixed to an aluminum sample stage with a tape having a carbon-containing adhesive on both faces, was subjected to platinum-palladium sputtering. The results of observation at an acceleration voltage of 5 kV are shown in FIGS. 3(A) to 3(C). Without crosslinking treatment, no enzyme protein adsorption layer was observed after 5 cycles of washing, demonstrating the enzyme protein was desorbed from the fiber surface. With glutaraldehyde or DENACOL EX-521 crosslinking, an enzyme protein adsorption layer was present even after 20 cycles of washing, supporting the results shown in Table 2.

Example 3

The cotton fiber treated as in Example 2, and, as controls, a cotton fiber without crosslinking treatment and a cotton fiber without any treatment were tested for hygroscopicity.

Figure 4:
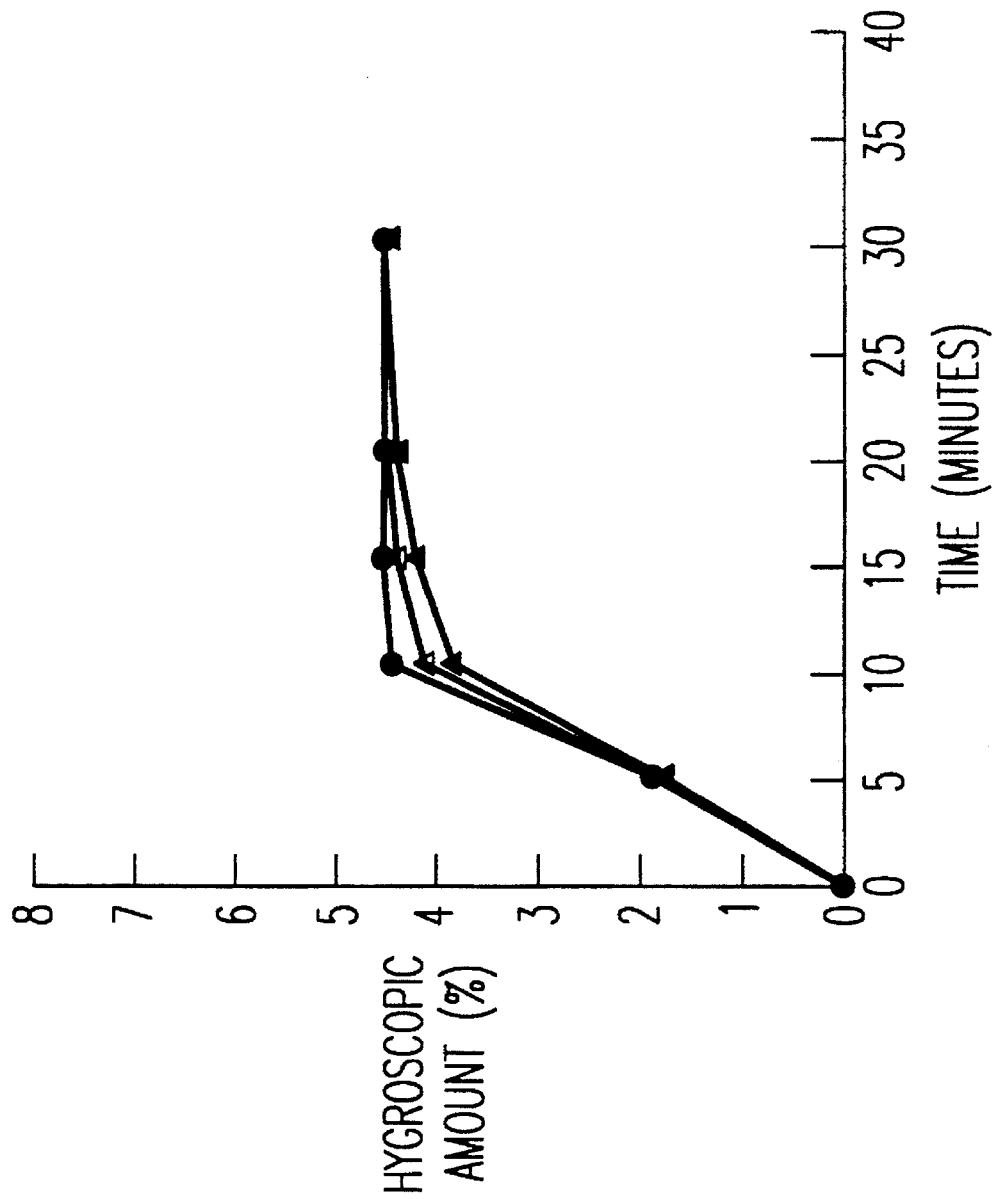
FIG. 4 is a graph showing time-course change in the amount of moisture taken up by fibers in Example 3, wherein ● represents an untreated fiber; ▲ represents a fiber crosslinked with glutaraldehyde; and △ represents a fiber crosslinked with DENACOL EX-521.

The hygroscopicity of the fibers was measured as follows: the fiber was dried at 105° C. for 3 hours in a dryer; the dried fiber was allowed to stand at 40° C. at 80% RH; and hygroscopic rate and saturated hygroscopic amount were determined by measuring the time-course change in fiber weight due to moisture absorption. The results are shown in FIG. 4. As obvious from FIG. 4, the cotton fiber treated according to the present invention are comparable to untreated fibers with respect to hygroscopic rate and saturated hygroscopic amount.

Example 4

The cotton fiber treated as in Example 2, and, as controls, a cotton fiber without crosslinking treatment and a cotton fiber without any treatment were tested for durability of the single fiber against external physical stimulation. Water flow of washing machine was employed as the external physical stimulation, and the damage to the fiber (fuzz on the surface of a single fiber) after 20 cycles of washing was observed in the same manner as in Example 2. FIGS. 5(A) and 5(B) are microphotographs of the fiber surface. As shown in FIG. 5(A), fuzz occurs to a high degree on the surface of the untreated fiber, the fuzz being entangled between monofilaments, while only a slight degree of fuzz occurs on the surface of a single fiber treated to have an enzyme protein adsorption layer as shown in FIG. 5(B).

Example 5 (Inventive Examples 1 and 2, Comparative Examples 1 to 3)

The specific surface area of a fiber was calculated by the BET multiple-point method based on krypton adsorption. Specifically, BELSORP36, a full-automatic gas adsorption apparatus manufactured by BEL JAPAN INC. was used under the following conditions: adsorption gas: krypton (purity: 99.995%); dead volume filling gas: helium (purity: 99.9999%); adsorption temperature: 77 K.; and measurement range of relative pressure: 0.01 to 0.35 (measuring pressure/saturated vapor pressure of adsorption gas). The time to an equilibrium was set at 180 seconds for each relative pressure, and a specific surface area was calculated on the basis of the BET (Brunauer-Emmett-Teller) theory. The specific surface area of a viscose rayon cloth (plain weave, manufactured by Teijin) was 0.202 m$^2$/g.

The enzyme proteins used were cellulase (molecular weight by SDS-PAGE: 100,000 and 130,000) produced by a Bacillus species (FERM-BP 1485) and cellulase (molecular weight by SDS-PAGE: 30,000 to 40,000; Meicelase TP-60, MeijiSeika Co., Ltd.) produced by a Trichoderma species and amylase (molecular weight by SDS-PAGE: 50,000 and 220,000) produced by a Bacillus species (FERM-BP 3048), all of them being used after ammonium sulfate precipitation, dialysis and lyophilization. The viscose rayon as mentioned above was used as a regenerated cellulose fiber. To remove textile oil, the regenerated fiber cloth was subjected to Soxhlet extraction for 6 hours using a mixture solvent of chloroform and methanol (1:1).

The buffers used were 100 mM acetic acid-sodium acetate buffer (pH 5, special grade, Wako Pure Chemical Industries, Ltd.), with an ionic strength adjusted at 0.1.

First, each enzyme protein was diluted with buffer. Protein concentrations were set within the range of 0–1 g/L, as converted to bovine serum albumin as determined by the Lowry method. Next, the fiber, 50 g per liter of a protein solution, was completely immersed in the solution. While the solution was shaken at 5° C., immersion was continued until an adsorption equilibrium was reached. The adsorption isotherm is shown in FIG. 6 (data on cellulase produced by a Bacillus sp.). By plotting adsorption isotherm, the following values were obtained as the amounts at adsorption equilibrium of Bacillus cellulase, Trichoderma cellulase, and Bacillus amylase to a viscose rayon cloth.

TABLE 3

| Enzyme protein | Amount at adsorption equilibrium (mg/m$^2$) |
| --- | --- |
| Cellulase of Bacillus sp. | 7.4 |
| Cellulase of Trichoderma sp. | 6.4 |
| Amylase of Bacillus sp. | 7.0 |

The same crosslinking agents as used in Example 2 were used. Specifically, glutaraldehyde (about 25% solution, 1st grade, Wako Pure Chemical Industries, Ltd.), an aldehyde-series crosslinking agent, and polyglycerol polyglycidyl ether (DENACOL EX-521, Nagase Chemicals Ltd.), an epoxy-series crosslinking agent, were used. Each crosslinking agent was diluted to make a 100 mM solution with acetic acid-sodium acetate buffer; the fiber, previously adsorbed with an enzyme protein, was immersed in the diluted solution of the crosslinking agent at 50 g per liter of the solution.

The glutaraldehyde solution was shaken at 20° C. for 1 hour to carry out the crosslinking reaction. The DENACOL EX-521 solution was heated from 20° C. to 90° C. within 10 minutes, followed by 1 hour of shaking to carry out the reaction. After completion of the crosslinking treatment, the fiber was thoroughly washed with water and dried.

Inventive Example 1 was a viscose rayon cloth having a Bacillus cellulase adsorption layer on the monofilament surface thereof, the layer being formed by immersing the cloth in a solution of Bacillus cellulase until an adsorption equilibrium was reached, and carrying out a crosslinking reaction with glutaraldehyde (100 mM) for 1 hour at room temperature; Inventive Example 2 was a viscose rayon cloth having a Bacillus cellulase adsorption layer on the monofilament surface thereof, the layer being formed in the same manner as for Inventive Example 1 except that a crosslinking reaction was carried out at 90° C. for 1 hour using DENACOL EX-521 (100 mM); Comparative Example 1 was a viscose rayon cloth having no protein adsorption layer; Comparative Example 2 was a viscose rayon cloth having a Bacillus cellulase adsorption layer on the monofilament surface thereof, the layer being formed in the same manner as for Inventive Example 1 except that the cloth was thoroughly washed with water and dried without carrying out crosslinking reaction after an adsorption equilibrium was reached; and Comparative Example 3 was a viscose rayon cloth having a Bacillus cellulase adsorption layer on the monofilament surface thereof, the layer being formed in the same manner as for Inventive Example 1 except that the cloth was heated at 90° C. for 1 hour without carrying out crosslinking reaction after an adsorption equilibrium was reached, then thoroughly washed with water and dried.

With the differently treated above examples, the feeling and touch, degree of fibrillation, and stability of the protein layer were tested by subjecting the examples to washing with a household washing machine using a model detergent having the same composition as used in Example 2.

The detergent was dissolved in tap water at 0.0833% (w/v). At a bath ratio to fiber of 1:30, the fiber was washed at 20° C. for 12 minutes using a household washing machine (SHIZUKA GOZEN manufactured by Hitachi, Ltd.), followed by 5 minutes of rinsing, dehydration and drying. This washing process was repeated in 20 cycles.

A sensory test was performed by comparing the feeling and touch of each cloth after 20 cycles of washing with Comparative Example 1 before washing. The feeling and touch were evaluated according to the following criteria:
(Evaluation criteria)

o: Better than Comparative Example 1 before washing

Δ: Equal to Comparative Example 1 before washing x: Worse than Comparative Example 1 before washing The surface of the monofilament of the cloth fiber was observed by a scanning electron microscopy (field emission scanning electron microscope, FE-SEM S-4000, Hitachi, Ltd.) at an acceleration voltage of 5 kV to evaluate the degree of fibrillation according to the criteria as shown below. Before observation, the cloth was subjected to platinum-palladium sputtering. The results are shown in Table 4.
(Evaluation criteria)

o: No fibrillation on the monofilament surface

Δ: Slight fibrillation on the monofilament surface x: Marked fibrillation on the monofilament surface The enzyme protein layer formed by adsorption was tested for its durability against washing by dyeing the cloth examples before and after washing with a dye for protein, Coomassie Brilliant Blue (Quick CBB for electrophoresis, Wako Pure Chemical Industries, Ltd.), and comparing the dyeability before and after washing to know the amount of residual protein from the difference in dyeability evaluated according to the following criteria:
(Evaluation criteria)

⊚: dyeability almost equal to the dyeability before washing o: dyeability slightly lower than the dyeability before washing Δ: dyeability markedly lower than the dyeability before washing x: no dyeability (equal to the dyeability of Comparative Example 1 before washing)

The feeling and touch of Inventive Examples 1 and 2, the regenerated cellulose fibers treated according to the present method, were retained after repeated washing. This may be because the enzyme protein layer adsorbed onto the monofilament surface, with its high durability against washing, prevents fuzz and hardening of fibers by suppressing fibrillation, and keeps the feeling and touch of the cloth for a long period of time.

Example 6 (Inventive Examples 3 and 4, Comparative Examples 4 to 6)

A polyester cloth (plain weave X-2200, manufactured by Asahi Kasei) was used as a synthetic fiber. The polyester cloth was treated in the same manner as in Example 5. To remove textile oil, the cloth was subjected to 6-hour Soxhlet extraction using a mixture solvent of chloroform and methanol (1:1). The specific surface area of the fiber was 0.205 $m^2/g$ as calculated by the BET multiple-point method based on krypton adsorption.

FIG. 7 shows the adsorption isotherm of the protein enzyme to the polyester cloth (data on cellulase produced by a Bacillus sp.). From the adsorption isotherm plotting, the values in Table 5 were obtained as equilibrium adsorption amounts of Bacillus cellulase, Trichoderma cellulase, and Bacillus amylase to the polyester cloth:

TABLE 5

| Enzyme protein | Amount at adsorption equilibrium (mg/m$^3$) |
| --- | --- |
| Cellulose of Bacillus sp. | 5.9 |
| Cellulase of Trichoderma sp. | 3.4 |
| Amylase of Bacillus sp. | 5.0 |

Inventive Example 3 was a polyester cloth having a Bacillus cellulase adsorption layer on the monofilament surface thereof, the layer being formed by immersing the cloth in a solution of Bacillus cellulase until an adsorption equilibrium was reached, and carrying out a crosslinking reaction with glutaraldehyde (100 mM) for 1 hour at room temperature; Inventive Example 4 was a polyester cloth having a Bacillus cellulase adsorption layer on the monofilament surface thereof, the layer being formed in the same manner as for Inventive Example 3 except that a crosslinking reaction was carried out at 90° C. for 1 hour using DENACOL EX-521 (100 mM); Comparative Example 4 was a polyester cloth having no protein adsorption layer; Comparative Example 5 was a polyester cloth having a Bacillus cellulase adsorption layer on the monofilament surface thereof, the layer being formed in the same manner as for Inventive Example 3 except that the cloth was

TABLE 4

| | | Feel · Touch | | | Durability of enzyme protein layer against washing |
| --- | --- | --- | --- | --- | --- |
| | Crosslinking agent | Before washing | After washing | Fibrillation | |
| Comparative Examples 1 | No crosslinking/No adsorption | Δ | x | x | x |
| Comparative Examples 2 | No crosslinking | o | x | x | x |
| Comparative Examples 3 | Heating, No crosslinking | o | x | Δ | Δ |
| Inventive Examples 1 | Glutaraldehyde | o | o | o | o |
| Inventive Examples 2 | DENACOL EX-521 | o | o | o | ⊚ |

When cellulase produced by a Trichoderma sp. or amylase produced by a Bacillus sp. was used as the enzyme protein, similar results were obtained.

thoroughly washed with water and dried without carrying out crosslinking reaction after an adsorption equilibrium was reached; and Comparative Example 6 was a polyester cloth having a Bacillus cellulase adsorption layer on the monofilament surface thereof, the layer being formed in the same manner as for Inventive Example 3 except that the cloth was heated at 90° C. for 1 hour without carrying out crosslinking reaction after an adsorption equilibrium was reached, then thoroughly washed with water and dried.

The cloth examples above were subjected to washing in the same manner as in Example 5, and a sensory test for feeling and touch was performed similarly to Example 5 according to the evaluation criteria below.

(Evaluation criteria)
- o: Better than Comparative Example 4 before washing
- Δ: Equal to Comparative Example 4 before washing
- x: Worse than Comparative Example 4 before washing The hygroscopic property of the examples was tested as follows: the cloth to be tested was allowed to stand for 2 hours at 20° C. and 65% RH or at 20° C. and 90% RH, and the weight of the cloth was measured (weight A); then the cloth was perfectly dried at 105° C. for 2 hours, and the weight of the cloth was measured (weight B); and the hygroscopic rate of the cloth was calculated by applying the values A and B to the following equation:

$$\text{Hygroscopic rate (\%)} = (A-B)/B \times 100$$

The results are given in Table 6.

The enzyme protein adsorption layer was tested for its durability against washing by dyeing the cloth examples before and after washing with a dye for protein, Coomassie Brilliant Blue (Quick CBB for electrophoresis, Wako Pure Chemical Industries, Ltd.), and comparing the dyeability before and after washing to know the amount of residual protein from the difference in dyeability evaluated according to the following criteria:

(Evaluation criteria)
- ⊚: dyeability almost equal to the dyeability before washing
- o: dyeability slightly lower than the dyeability before washing
- Δ: dyeability markedly lower than the dyeability before washing
- x: no dyeability (equal to the dyeability of Comparative Example 4 before washing)

The feeling and touch of Inventive Examples 3 and 4, wherein the synthetic fibers treated according to the present method, were found to be improved. This may be because the enzyme protein layer adsorbed onto the monofilament surface provides a synthetic fiber with high hygroscopicity. This effect is expected to last long with high durability of the protein adsorption layer against washing.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A fiber for clothing, said fiber having a layer of crosslinked enzyme protein on a surface of a monofilament thereof, wherein said fiber is selected from the group consisting of a natural cellulose fiber, a regenerated cellulose fiber and a synthetic fiber, and wherein said layer of crosslinked enzyme protein is formed by crosslinking with a compound selected from the group consisting of an epoxy compound and an isocyanate compound.

2. The fiber for clothing according to claim 1, wherein said enzyme protein is hydrolase.

3. The fiber for clothing according to claim 1, wherein said natural cellulose fiber is cotton or hemp.

4. The fiber for clothing according to claim 1, wherein said regenerated cellulose fiber is viscose rayon.

5. The fiber for clothing according to claim 1, wherein said synthetic fiber is selected from the group consisting of polyester, acrylic, nylon, polyvinylalcohol polypropylene, polyethylene, polyvinyl chloride, vinylidene, polyurethane, and benzoate.

6. The fiber for clothing according to claim 1, wherein said enzyme is selected from the group consisting of hydrolases, lyases, oxidoreductases, ligases, transferases and isomerases.

7. The fiber for clothing according to claim 5, wherein said enzyme is selected from the group consisting of peptidase, cellulase, amylase and lipase.

TABLE 6

| | | Feeling · Touch | | Hygroscopicity (%) | | | | Durability of |
| | | | | 20° C., 65% RH | | 20° C., 65% RH | | enzyme protein |
| | Crosslinking agent | Before washing | After washing | Before washing | After washing | Before washing | After washing | layer against washing |
| --- | --- | --- | --- | --- | --- | --- | --- | --- |
| Comparative Examples 4 | No crosslinking/No adsorption | Δ | x | 0.45 | 0.45 | 0.65 | 0.65 | x |
| Comparative Examples 5 | No crosslinking | o | x | 0.65 | 0.45 | 1.00 | 0.65 | x |
| Comparative Examples 6 | No crosslinking, heating | o | x | 0.65 | 0.45 | 1.00 | 0.65 | Δ |
| Inventive Examples 3 | Glutaraldehyde | o | o | 0.65 | 0.65 | 1.05 | 1.05 | o |
| Inventive Examples 4 | DENACOL EX-521 | o | o | 0.70 | 0.70 | 1.10 | 1.10 | ⊚ |

When cellulase produced by a Trichoderma sp. or amylase produced by a Bacillus sp. was used as the enzyme protein, similar results were obtained.

8. The fiber for clothing according to claim 1, wherein said epoxy compound is selected from the group consisting of mono- and poly-glycidyl ethers of ethylene glycol, polyethylene glycol, propylene glycol, polypropylene glycol, glycerol, sorbitol, polyglycerol, pentaerythritol, tris(2-hydroxyethyl)isocyanurate, trimethylolpropane, neopentylglycol, phenol ethylene oxide, lauryl alcohol ethylene oxide, lauryl alcohol ethylene oxide and epoxy-group-containing coupling agents.

9. The fiber for clothing according to claim 1, wherein said isocyanate compound is selected from the group consisting of toluene diisocyanate, diphenylmethane diisocyanate, hexamethylene diisocyanate, isophorane diisocyanate and naphthalene diisocyanate.

* * * * *